United States Patent
Shani et al.

(10) Patent No.: US 9,220,583 B2
(45) Date of Patent: Dec. 29, 2015

(54) DENTAL CARE DEVICE FOR DETECTION AND REMOVAL OF PLAQUE

(71) Applicants: Yuval Shani, Carcur (IL); Gil Weisman, Kibutz Hanita (IL); Tamir Ygal, Eschar (IL); Shlomi Gadol, Haifa (IL); Assaf Avram, Petach-Tikva (IL)

(72) Inventors: Yuval Shani, Carcur (IL); Gil Weisman, Kibutz Hanita (IL); Tamir Ygal, Eschar (IL); Shlomi Gadol, Haifa (IL); Assaf Avram, Petach-Tikva (IL)

(73) Assignee: Plaqless LTD, Yoqneam (IL)

( * ) Notice: Subject to any disclaimer, the term of this patent is extended or adjusted under 35 U.S.C. 154(b) by 99 days.

(21) Appl. No.: 14/059,689

(22) Filed: Oct. 22, 2013

(65) Prior Publication Data

US 2015/0107034 A1    Apr. 23, 2015

(51) Int. Cl.
| | |
|---|---|
| *A61C 17/22* | (2006.01) |
| *A46B 15/00* | (2006.01) |
| *A61B 5/00* | (2006.01) |
| *A61C 17/34* | (2006.01) |

(52) U.S. Cl.
CPC ........... *A61C 17/221* (2013.01); *A46B 15/0004* (2013.01); *A46B 15/0006* (2013.01); *A46B 15/0016* (2013.01); *A46B 15/0038* (2013.01); *A61B 5/0088* (2013.01); *A61C 17/349* (2013.01); *A46B 15/004* (2013.01); *A61C 17/3436* (2013.01)

(58) Field of Classification Search
CPC ........ A46B 13/00; A46B 13/02; A46B 15/00; A46B 15/0002; A46B 15/0004; A46B 15/0006; A61C 17/00; A61C 17/16; A61C 17/22; A61C 17/221; A61C 17/32; A61C 17/3409–17/349

USPC ............................ 15/22.1, 22.2, 22.4, 23, 28
See application file for complete search history.

(56) References Cited

U.S. PATENT DOCUMENTS

| | | | | |
|---|---|---|---|---|
| 5,894,620 | A * | 4/1999 | Polaert et al. | ........... 15/22.1 |
| 6,685,471 | B1 * | 2/2004 | Kawamura et al. | ......... 433/29 |
| 2005/0003323 | A1 | 1/2005 | Katsuda et al. | |

(Continued)

FOREIGN PATENT DOCUMENTS

| | | |
|---|---|---|
| WO | WO2013/001462 | 1/2013 |
| WO | WO/2013/027462 | 2/2013 |

OTHER PUBLICATIONS

International Search Report dated Jan. 4, 2015; International Application No. PCT/IL2014/050852; International Filing Date: Sep. 29, 2014; 6 pages.

(Continued)

*Primary Examiner* — Mark Spisich
(74) *Attorney, Agent, or Firm* — Blank Rome LLP

(57) ABSTRACT

The present invention relates to a dental care device for detection and removal of plaque automatically and independently, comprising: a) a motion controlled and pressure sensitive plaque removal head having at least one array of bristles; b) a plaque detection unit adapted to capture images of the teeth and gums, wherein said plaque detection unit includes an imaging device and a light source with specific wavelength for illumination said teeth and gums; and c) a plaque detection engine adapted to process the captured images in order to detect plaque infected areas on said teeth, and accordingly to generate instructions for automatically guiding said motion controlled plaque removal head, thereby executing all the necessary movements for automatically and independently removing the plaque from said teeth while minimizing abrasiveness by controlling the pressure applied and avoiding brushing to clean areas of the teeth and gums.

19 Claims, 7 Drawing Sheets

(56) References Cited

U.S. PATENT DOCUMENTS

| | | |
|---|---|---|
| 2005/0155168 A1 | 7/2005 | Hohlbein |
| 2008/0060148 A1* | 3/2008 | Pinyayev et al. ............... 15/22.1 |
| 2009/0056044 A1* | 3/2009 | Rizoiu et al. .................... 15/22.1 |
| 2011/0314618 A1 | 12/2011 | Binner et al. |
| 2012/0171657 A1 | 7/2012 | Ortins et al. |
| 2012/0295216 A1 | 11/2012 | Dykes et al. |
| 2013/0061412 A1* | 3/2013 | Vashi ............................... 15/106 |
| 2013/0203008 A1* | 8/2013 | Kressman et al. .............. 433/27 |

OTHER PUBLICATIONS

Written Opinion dated Jan. 4, 2015; International Application No. PCT/IL2014/050852; International Filing Date: Sep. 29, 2014; 7 pages.

English translation; International Published Application No. WO2013/027462 extending from PCT/JP2012/064626.

* cited by examiner

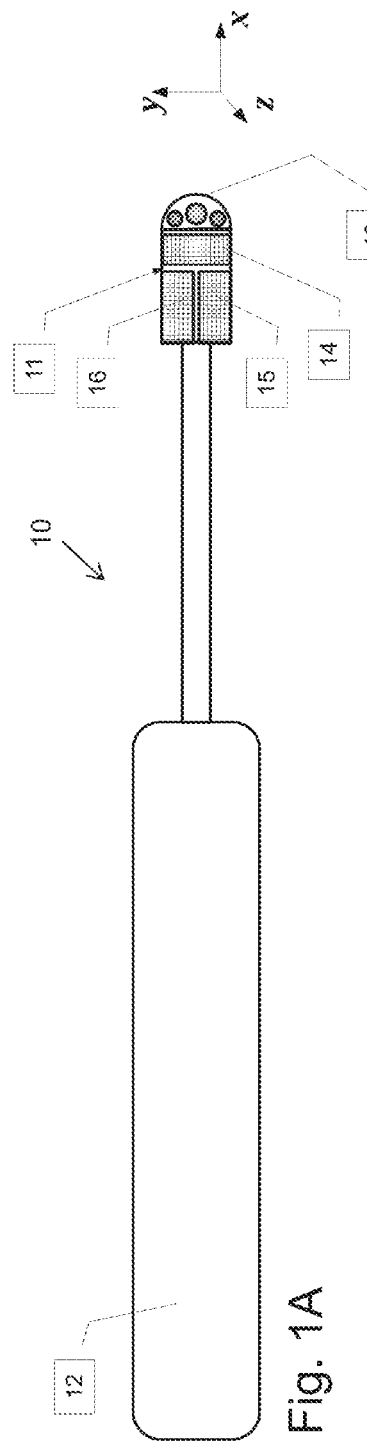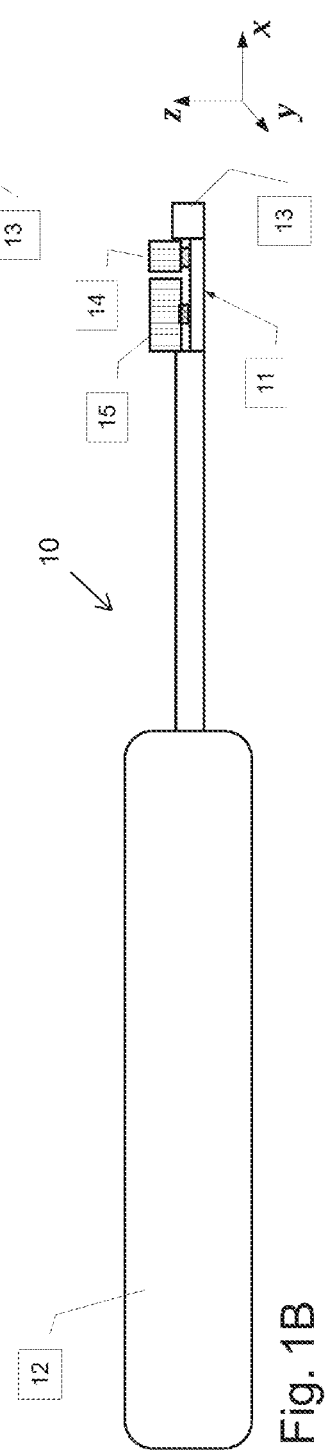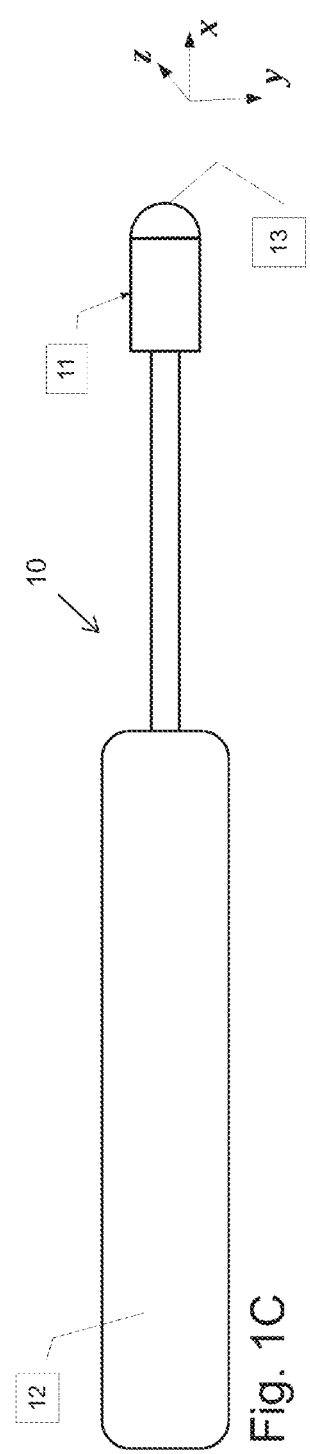

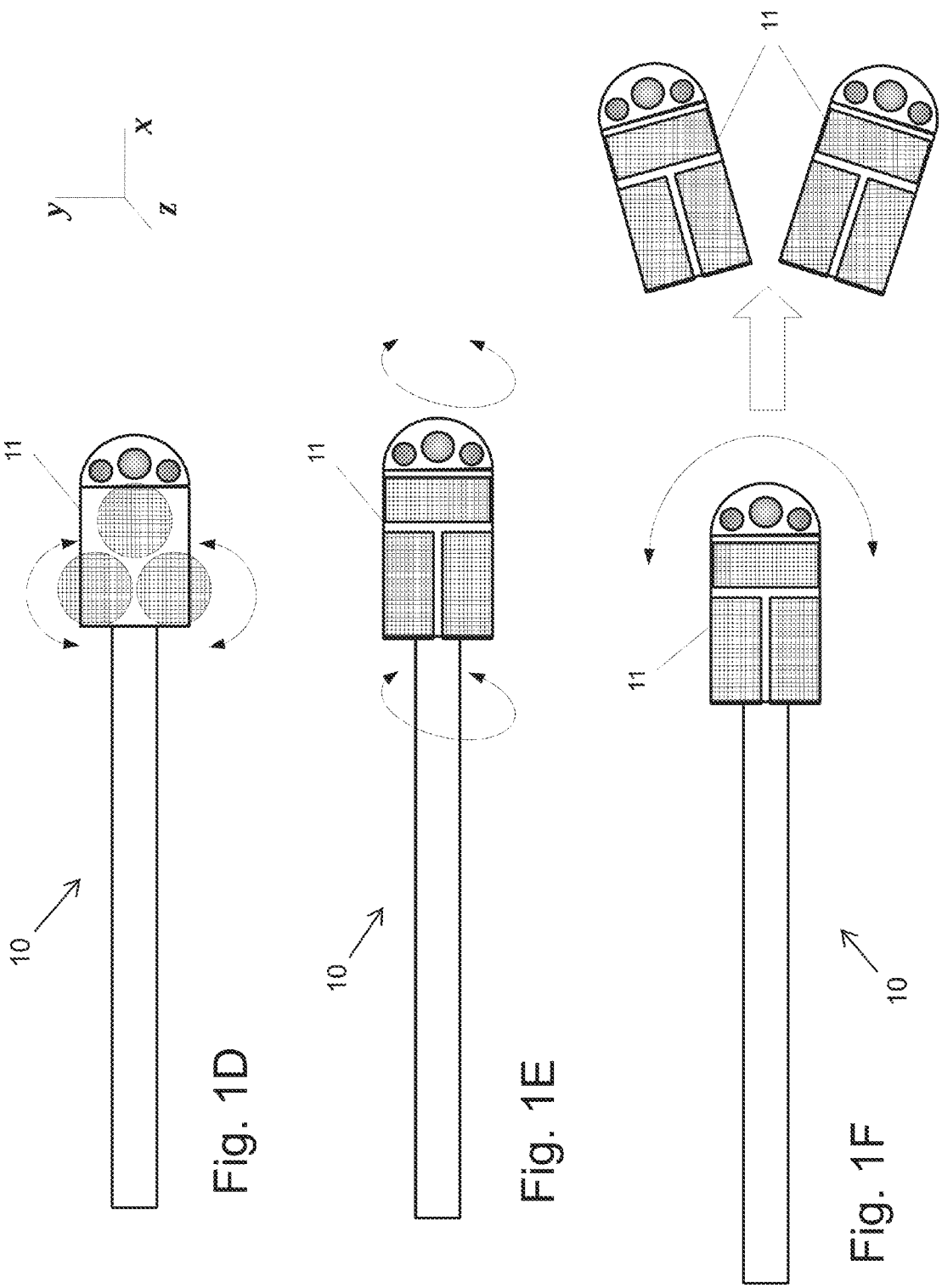

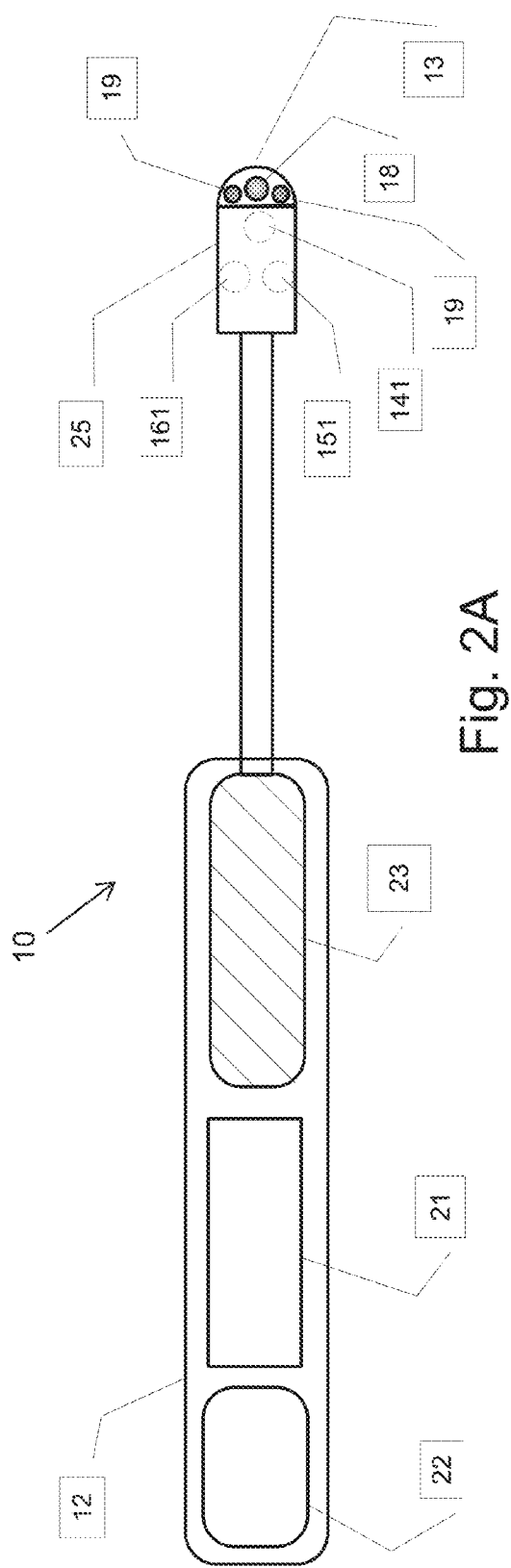
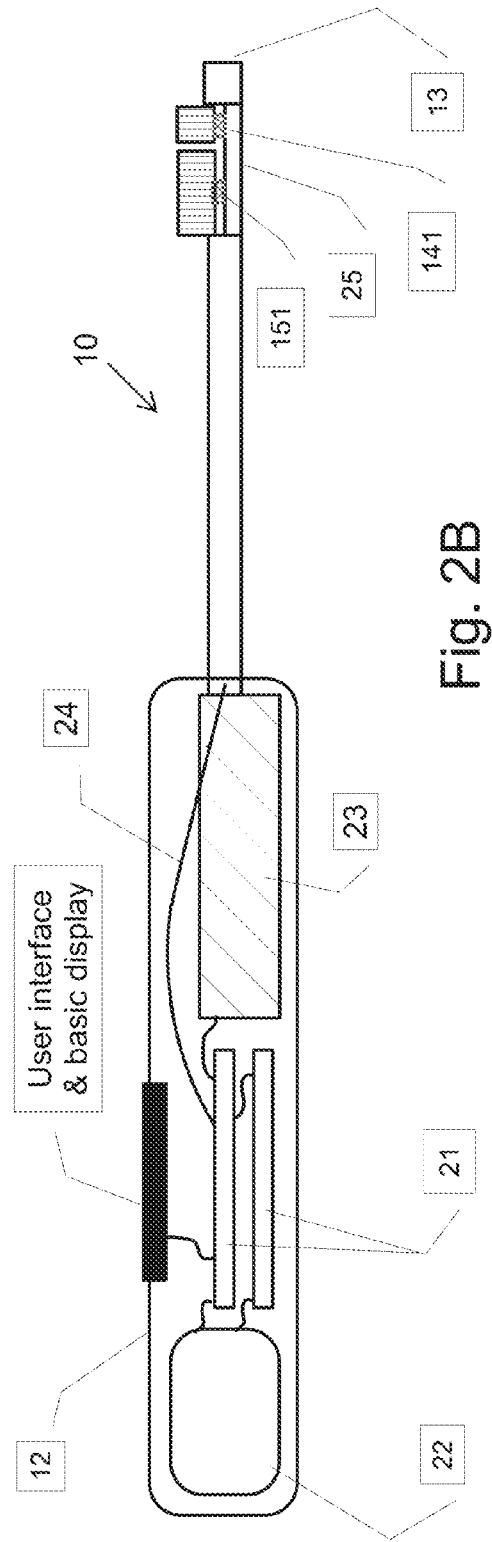
Fig. 2A
Fig. 2B

Top view

Side view

DENTAL CARE DEVICE FOR DETECTION AND REMOVAL OF PLAQUE

FIELD OF THE INVENTION

The present invention relates to the field of dental care devices. More particularly, the invention relates to an electric motorized toothbrush that focuses on plaque infected areas for efficient and comprehensive brushing.

BACKGROUND OF THE INVENTION

The use of electrical powered toothbrushes for cleansing teeth is well known. Typically these toothbrushes employ some kind of rotating head able to perform semi-circular or vibrating motions, a brush handle with a hollow space to place batteries, a motorized element and some kind of user interface (either switch buttons or a small user screen). These components together build an electrical toothbrush but they work separately and without any knowhow or knowledge collection. The existing toothbrushes blindly operate based on the user placement in the mouth and regardless if the specific location requires cleaning or more comprehensive plaque treatment.

The existing toothbrushes boast the fact that their movable head performs faster and faster circular repetitions but ignore the fact that this can be abrasive to the teeth and gums. Accordingly it is desired to provide an improved electric motorized toothbrush that overcomes the shortcomings described above by automatically detecting the plaque infected areas and furthermore by controlling and monitoring the movements and applied pressure of the brush head to work specifically on the detected areas and prevent abrasiveness to the teeth and gums. Closing the loop between understanding where the plaque resides and enabling the brush head to reach these areas without user intervention enables comprehensive and efficient brushing which is the basis of Smart brushing.

It is an object of the present invention to provide a dental care device that automatically detects the plaque infected areas.

It is another object of the present invention to provide a dental care device that is capable of controlling and monitoring the brush head to work specifically on the plaque detected areas.

It is yet another object of the present invention to provide a dental care device that eliminates unnecessary abrasiveness to the teeth and gums.

Other objects and advantages of the invention will become apparent as the description proceeds.

SUMMARY OF THE INVENTION

The present invention relates to a dental care device for detection and removal of plaque automatically and independently, comprising:
  a. a motion controlled and pressure sensitive plaque removal head having at least one array of bristles;
  b. a plaque detection unit adapted to capture images of the teeth and gums, wherein said plaque detection unit includes an imaging device and a light source with specific wavelength for illumination said teeth and gums; and
  c. a plaque detection engine adapted to process the captured images in order to detect plaque infected areas on said teeth, and accordingly to generate instructions for automatically guiding said motion controlled plaque removal head, thereby executing all the necessary movements for automatically and independently removing the plaque from said teeth while minimizing abrasiveness by controlling the pressure applied and avoiding brushing to clean areas of the teeth and gums.

According to an embodiment of the invention, the plaque detection unit is programmed to operate by applying hardware and/or software plaque finder algorithm(s).

According to an embodiment of the invention, the plaque finder algorithm involves image processing, edge detection, object detection and proprietary algorithm based on the deflected wavelength produced by the illumination process.

According to an embodiment of the invention, the dental care device further comprises a user information processor for providing user video/audio indications while using said device.

According to an embodiment of the invention, the user indication includes real time brushing indications when user is asked to place the brush in a new location, timer, quality of brushing, percentage of plaque and over time improvement.

According to an embodiment of the invention, the dental care device further comprises two or more linear arrays of bristles, such that a first array of bristles is positioned in a vertical orientation with respect to the other arrays of bristles, thereby providing two or more degrees of freedom.

According to an embodiment of the invention, the array of bristles is formed in a rounded manner, a linear manner or combination of both.

According to an embodiment of the invention, the plaque removal head is longer than standard and having at least one flexible joint for enabling adjusting the shape of the plaque removal head to match the teeth line and brush several teeth simultaneously and one or more sensor devices for plaque detection.

According to an embodiment of the invention, the movements of the flexible joints are passive and are depending only on the joint flexibility.

According to an embodiment of the invention, the movements of the flexible joints are active by using one or more motors or actuators.

BRIEF DESCRIPTION OF THE DRAWINGS

In the drawings:

FIG. 1A schematically illustrates a simplified front view of dental care device, according to an embodiment of the present invention;

FIG. 1B schematically illustrates a simplified side view of the dental care device of FIG. 1A;

FIG. 1C schematically illustrates a simplified back view of the dental care device of FIG. 1A;

FIGS. 1D-1F schematically illustrate possible movements of the plaque removal head of the dental care device, according to some embodiments of the present invention;

FIGS. 2A and 2B is an exemplary view of the internal elements of the dental care device of FIG. 1A, according to an embodiment of the present invention;

DETAILED DESCRIPTION OF THE INVENTION

Figure 3A:
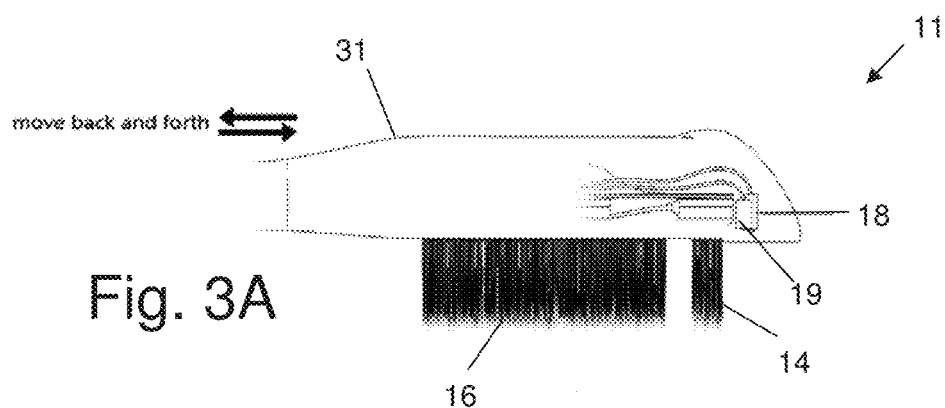
FIGS. 3A-3B schematically illustrate the head region of the dental care device applicable as an undercarriage performing the controlled automatic movements, according to an embodiment of the present invention.

The present invention is a dental care device that automatically detects plaque infected areas on the teeth and accordingly works to resolve them by controlling and monitoring the movements of a plaque removal element to reach and focus on the contaminated areas thus eliminating abrasive application of the brush by controlling the pressure applied and avoiding areas which do not need brushing enabling comprehensive and efficient cleaning in a shorter time. The dental care device does not imply any particular shape, construction material or geometry, and invention is applicable to all suitable devices that can be implemented in form of an electric motorized toothbrush-like device.

Reference will now be made to several embodiments of the present invention, examples of which are illustrated in the accompanying figures. Wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

While certain examples may refer to a dedicated dental care device, other devices can be used as well, such as a special toothbrush. The terms, "for example", "e.g.", "optionally", as used herein, are intended to be used to introduce non-limiting examples. While certain references are made to certain example system components, other components can be used as well and/or the example components can be combined into fewer components and/or divided into further components.

FIGS. 1A-1C show a dental care device that can be used in conjunction with the invention. The device generally indicated by numeral 10 in the figure is in form of an integrative electric motorized toothbrush that comprises a plaque removal head 11 and a body 12 in form of a handle. The body 12 and the head 11 are coupled in a way that allows movement of the head 11 in the linear axis.

The plaque removal head 11 is equipped with multiple arrays of bristles placed vertically and horizontally to accommodate the different brushing strokes needed in different areas of the tooth and gums. According to an embodiment of the invention, each array of bristles is controlled separately by a dedicated motor (e.g., each motor can be located on the head 11 itself, or elsewhere along the body of the dental care device 10 that will allow the motor to rotate/vibrate the bristles) thus all the combinations of operation (i.e., activating/deactivating each motor independently, accelerating or slowing by controlling the power and speed of each motor, more advance configuration may also allow to control the height or deflection of array of bristles, etc.) are applicable based on a plaque detection algorithm. Using a plurality of motors allows the bristles to move in any direction (i.e., two or more degrees of freedom).

As will be apparent to the skilled person, the plaque removal head 11 can be configured to move in variety of ways. According to some embodiments of the invention, each array of bristles rotates independently to both directions on the x-y plane, as shown with respect to FIG. 1D. In another embodiment, the whole plaque removal head 11 rotates to both directions around the x axis, as shown with respect to FIG. 1E. In another embodiment, the whole plaque removal head 11 rotates to both directions around the z axis (i.e., head 11 move right or left), as shown with respect to FIG. 1F. In this embodiment, the pivot point can be anywhere along the head 11, arm, or the body of device 10.

According to an embodiment of the invention, back and forth movements of the head 11 are controlled by an additional motor (e.g., a linear actuator that can be placed in the body 12 of the dental care device 10). Any suitable motor can be used to control these movements based on the chosen embodiment and implementation. The plaque removal head 11 is equipped with a sensor module such as an imaging device (e.g., a tiny camera), a line scanner, or other optical means, which takes a stream of continues visual data (e.g., images) of the specific area the plaque removal head 11 is located at, and sends the data to a processing unit.

According to an embodiment of the invention, the plaque removal head 11 comprises a plaque detection unit 13 and means that facilitates the cleansing of the teeth and gums, such as one or more arrays of tightly clustered bristles, e.g., as indicated by numerals 14-16. In this exemplary implementation, the head 11 is equipped with, but not limited to, an array of horizontal tightly clustered bristles 14 and two arrays of vertical tightly clustered bristles 15 and 16. Optionally, an array of round tightly clustered bristles can also be employed (not shown). FIGS. 1B and 1C show a side and a back view in accordance with the present invention and correlated to FIG. 1A.

FIGS. 2A and 2B show views of the elements of the dental care device in accordance with an embodiment of the present invention. In this configuration, the arrays of bristles 14-16 reside on a chassis 25, holding the bristles (e.g., on the top side) and a dedicated motor for each array of bristles (e.g., on the other side), respectively as indicated by numeral 141, 151 and 161. For example, the plaque detection unit 13 is located adjacent to the array of horizontal tightly clustered bristles 14 at the edge of head 11. FIG. 2A shows the dedicated motors 141, 151 and 161 without the array of bristles.

Figure 3B:
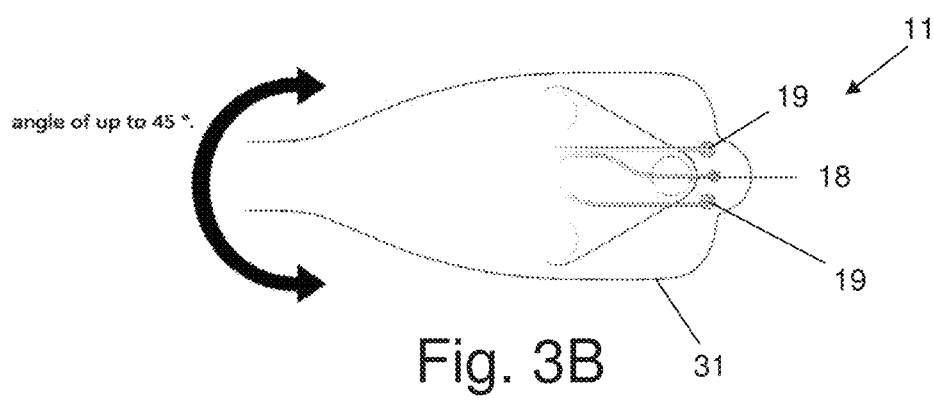

The plaque detection unit 13 includes a Plaque Detection Sensor (PDS) 18 (e.g., a camera) and a light source 19 (e.g., a LED) as shown in further details in FIGS. 3A and 3B. PDS 18 takes a continuous stream of images controlled by a plaque detection engine 21. Each image is being processed by the plaque detection engine 21 (e.g., in this embodiment the plaque detection engine 21 is placed in the body 12). For example, in this configuration, all the wiring for controlling each dedicated motor 141, 151 and 161 separately or passing data between the plaque detection unit 13 and the plaque detection engine 21 can be done in wired manner, e.g., through a set of wiring as generally indicated by numeral 24.

The plaque detection engine 21 receives a continuous stream of images and performs advanced picture processing algorithms on the received each image starting from image stabilization and stitching algorithms to compensate for jitter resulting from the fact that the device is hand held and through color transformation and object edge detection, as will be described in further details hereinafter with respect to FIGS. 4 and 5.

The result of the picture processing is a set of commands to control the next movement performed by each array of bristles 14-16 and the in conjunction with the movement of the head 11 along the x-axis. According to the command each dedicated motor 141, 151 and 161 can be activated, stopped, accelerated or slowed. Any combinations of the four dedicated motors 141, 151 and 161 are applicable, such as:

only the upper horizontal dedicated motor is working;
only the bottom horizontal dedicated motor is working;
both horizontal dedicated motors are working;
only the vertical dedicated motor is working;
only the upper horizontal dedicated motor and vertical dedicated motor are working;
only the bottom horizontal dedicated motor and vertical dedicated motor are working;
both horizontal dedicated motors and vertical dedicated motor are working;
only the round dedicated motor is working;
only the round dedicated motor and upper horizontal dedicated motor are working;
only the round dedicated motor and bottom horizontal dedicated motor are working;
only the round dedicated motor and both horizontal dedicated motors are working;
only the round dedicated motor and vertical dedicated motor are working;
only the round dedicated motor, upper horizontal dedicated motor and vertical dedicated motor are working;
only the round dedicated motor, bottom horizontal dedicated motor and vertical dedicated motor are working;
only the round dedicated motor, both horizontal dedicated motors and vertical dedicated motor are working.

Being able to control each dedicated motor separately with great precision allows efficient comprehensive brushing while minimizing abrasiveness to the clean teeth areas.

The plaque removal head 11 can perform a variety of movements according to the selected embodiment. Back and forth head movements are controlled by but not limited to a linear motor placed in the body 12 (e.g., a brush handle). According to an embodiment of the invention, the PDS 18 is kept clean from any obstacle (water, steam, foam, etc. . . . ) that can interfere with the camera vision and therefore deteriorate the picture's quality in any number of ways as detailed but not limited to a dedicated wiper (not shown) or any hydrophobic material covering the lens. For example, when the PDS 18 is not active it can be wiped clean by the dedicated wiper.

Another embodiment utilizes a plaque removal head equipped with two motorized arrays of bristles. Back and forth head movements are controlled by a dedicated motor placed in the brush handle. The array of bristle can be either round, rectangular or any other shape and are controlled separately by a separate dedicated motor. Both motors can be turned on or off or work completely separately according to the plaque detecting algorithm. Each array of bristles can be placed on the plaque removal head in such a way that they cover the entire tooth length and gum line. In this specific embodiment, the head angular movement up to 45° might be redundant.

According to an embodiment of the invention, the dental care device 10 comprises a screen output 22 that can be applied to serve many features and applications including but not limited to user indications such as timer, quality of brushing, percentage of plaque and over time improvement. Other applications can be directed to the children line of products including but not limited to gifs, games, score count. Yet another application can include but is not limited to a real time panoramic view of the entire mouth with color indications to the plaque location serving both the consumer and professional markets.

In another embodiment the plaque removal head 11 comprises an undercarriage head 31 that is connected to the body 12 (FIG. 1) in such a way that allows movements in the X-Axis, Y-Axis and Z axis (as shown with respect to FIGS. 3A and 3B). The movements of the undercarriage head 31 are fully controlled by the plaque detection engine 21 (FIG. 2) in the length and height of the area being cleaned. The plaque detection unit 13 (e.g., the camera and the LEDs) resides on the undercarriage head 31. In addition, a replaceable head holding the array of bristles can be connected to the undercarriage head 31 and can be controlled by a dedicated motor as described hereinabove. The array of bristles can be activated, stopped, accelerated or slowed completely independent and without any correlation to the undercarriage placement or movement.

Figure 4A:
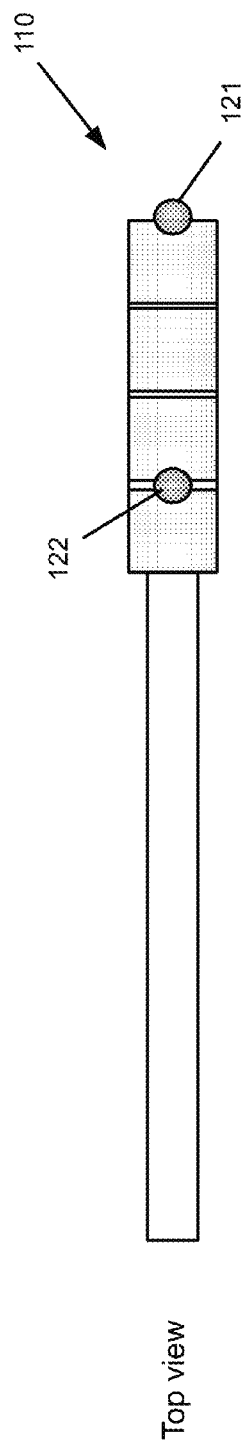
FIGS. 4A-4C, a plaque removal head with flexible joints is shown in accordance with another embodiment of the present invention.
Figure 4B:
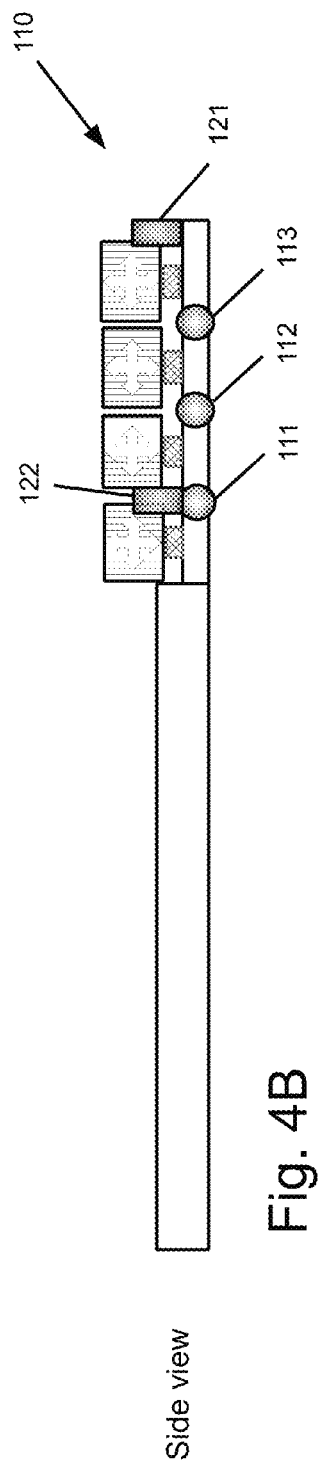
Figure 4C:
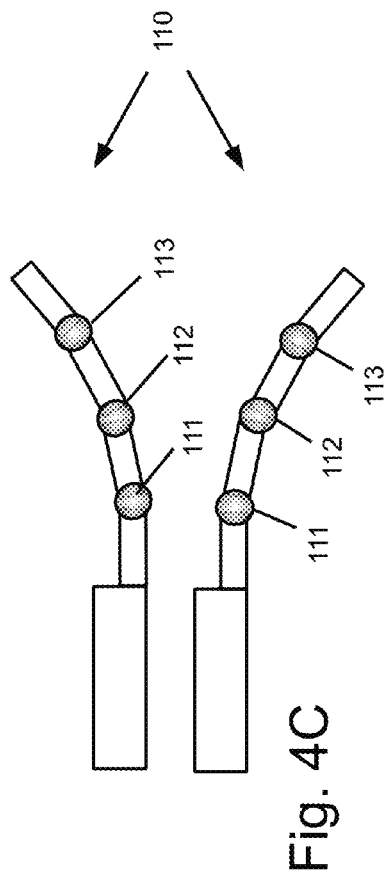

Referring now to FIGS. 4A-4C, a plaque removal head 110 with flexible joints is shown in accordance with another embodiment of the present invention. The plaque removal head 110 comprises one or more flexible joints, as indicated by numerals 111, 112 and 113. The flexible joints configuration enables adjusting the shape of the plaque removal head 110 to match the teeth line. Movement of joints around the Y axis can be passive (depending only on the joint flexibility) or active (using motors or actuators). In such configuration, the plaque removal head 110 may include more than one PDS as indicated by numerals 121 and 122.

The head 110 can maximize the brushing efficiency by dividing the mouth into larger areas (e.g., inside, outside and upside of the teeth topology) instead of having to brush teeth after teeth one by one. The entire plaque removal head 110 can still move on the x-axis utilizing a linear motor. Due to its length, the plaque removal head 110 covers a large area of the mouth. The PDS 121 and 122 relay the images to the plaque detector engine which only has to inform if cleaning is finished for the specific area being worked on (e.g., plaque exist=TRUE/FALSE) when the answer is FALSE and indication to the user is given (indication can be either beeping sound, vibration or any other means) to the user to move to the next location.

As will be appreciated by the skilled person the arrangement described in the figures results in a tool that applies Smart brushing. Equipped with a sensor and proprietary control logic running advanced algorithms, the integration of the sensor, dedicated motors and special logic enables closing the loop between detecting the plaque residing areas and controlling the plaque removal element to reach them, thereby providing a tool that applies a Smart brushing.

Smart brushing can be achieved by one or more of the methods listed but not limited to. One method merely requires the user to insert the dental care device into his mouth, making sure to leave the dental care device at a fixed location until an automatic user indication is asserted indicating to move to the next location and repeat this action as indicated by the dental care device. Another method may require the user to use a proprietary disclosing solution toothpaste or mouth wash before performing the actions described in the first method hereinabove. Yet another method may require the user to first scan the entire mouth enabling the dental care device to create a full mouth image thus enabling references to specific coordinates and location. Any of the methods described results in Smart brushing activating the advanced integrated logic and mechanics to remove more plaque from the teeth.

Turning now to the logical circuit, it is composed of a special logic that can be of many embodiments such as FPGA, ASIC, CPU, PU (Processing Unit) or any other programmable logic but not limited to and enables implementation of advanced algorithms. The generic algorithms can be used for multiple applications some of which but not limited to are plaque detection, tooth and mouth 2D and 3D dimensional pictures, health related alerts and more.

The processing unit, in any of the preferred embodiments utilizes an FPGA, ASIC, CPU, PU or other form of programmable logic which performs advanced picture processing algorithms on the received stream of images. The processing may involve the following tasks, but can be enhanced with alternative or additional tasks:

Primary picture processing starting from image stabilization and stitching algorithms to compensate for jitter resulting from the fact that the device is hand held followed by filtering, scaling, histogram construction and color manipulation;

Teeth boundary detection by object edge detection thus eliminating non relevant areas, threshold search and additional smoothing and filtering;

Specific plaque detection, looking for specific color deflection on the teeth boundaries detected earlier.

The result is a set of commands to control the next movement performed by the brush head in reference to the last coordinates the brush was at, controlling the on/off function of each motor separately and calculating the current location. In accordance to the long head with flexible joints embodiment there is no need to calculate new coordinates and the result is simply the existence of plaque=True or False.

According to an embodiment of the invention, plaque detection can be performed but not limited to one or all of the following ways:

Specific nanometer wavelength for plaque identification/coloring;

Proprietary disclosing solution tooth paste/mouth wash;

Proprietary algorithm for feature detection and object recognition.

The functions described herein may be performed by executable code and instructions stored in computer readable medium and running on a processor-based system that is implemented in the plaque detection engine 21. However, state machines, and/or hardwired electronic circuits can also be utilized. Further, with respect to the example processes described herein, not all the process states need to be reached, nor do the states have to be performed in the illustrated order.

Figure 5:
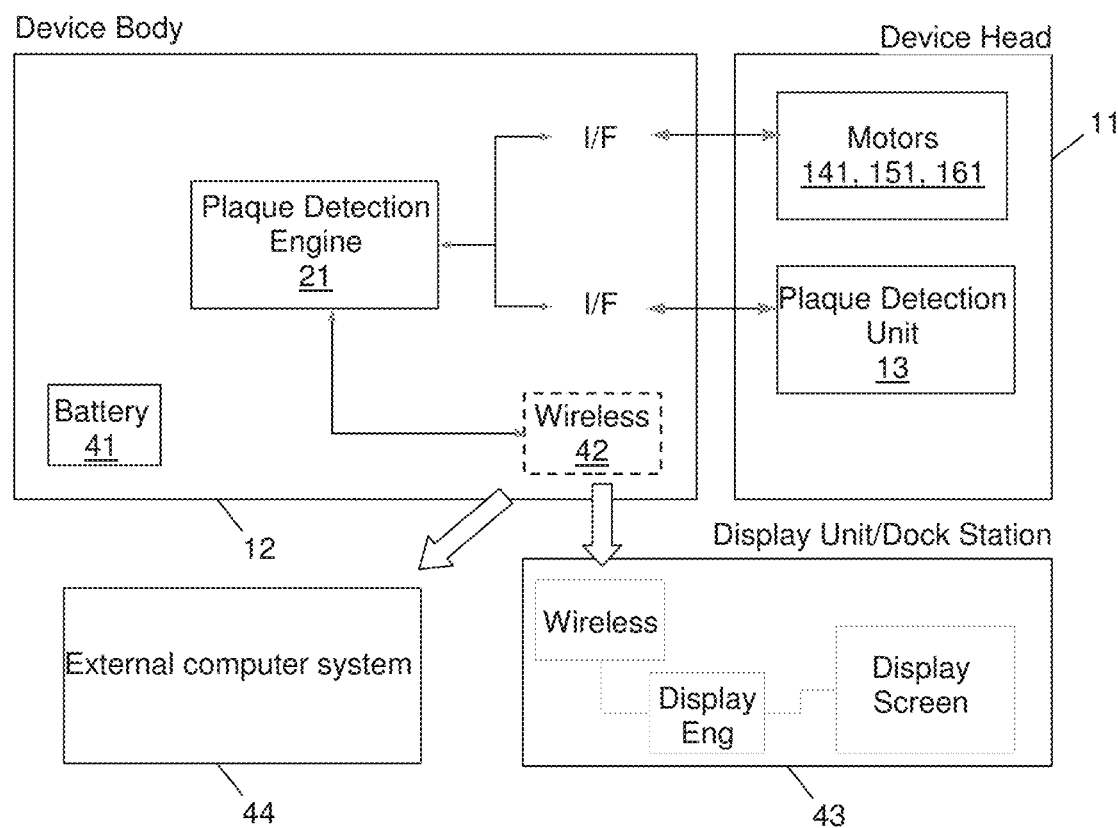
FIG. 5 schematically illustrates, in a block diagram form, the electrical components of the dental care device, according to an embodiment of the present invention.

FIG. 5 schematically illustrates, in a block diagram form, the electrical components of the dental care device 10 of FIG. 2, according to an embodiment of the present invention. The dental care device 10 includes the plaque detection engine 21, the plaque detection unit 13, the dedicated motor(s) such as 141, 151 and 161 and a power source, e.g., as indicated by battery 41.

According to an embodiment of the invention, the dental care device 10 may further include a communication port 42 (e.g., a wireless, a wired or combination of both) for allowing the dental care device 10 to forward data (either processed or raw) to external devices such as an external display unit 43, dock station, smartphones, notebooks or other computer based devices as generally indicated by numeral 44, etc. The communication port can be implemented by any suitable communication protocol such as a USB port, WiFi, Bluetooth and the like.

The Plaque Detection Engine (PDE) 21 performs all the video processing required for accurate analysis of the movement of the plaque removal head 11. The PDE 21 also performs the wireless/wired output to the external display unit 43 for displaying user information. As apparent to a person skilled in the art, the PDE 21 communicates with the motors 141, 151, 161 and with the PDU 13 via any suitable interface as indicated by "I/F" in the figure.

The PDE 21 is responsible for the very delicate sliding movement of the head 11 as well as on/off commands to each dedicated motor of each array of bristles in order to prevent abrasive tear of the tooth surface where no plaque resides.

All the above will be better understood through the following illustrative and non-limitative examples.

Figure 6:
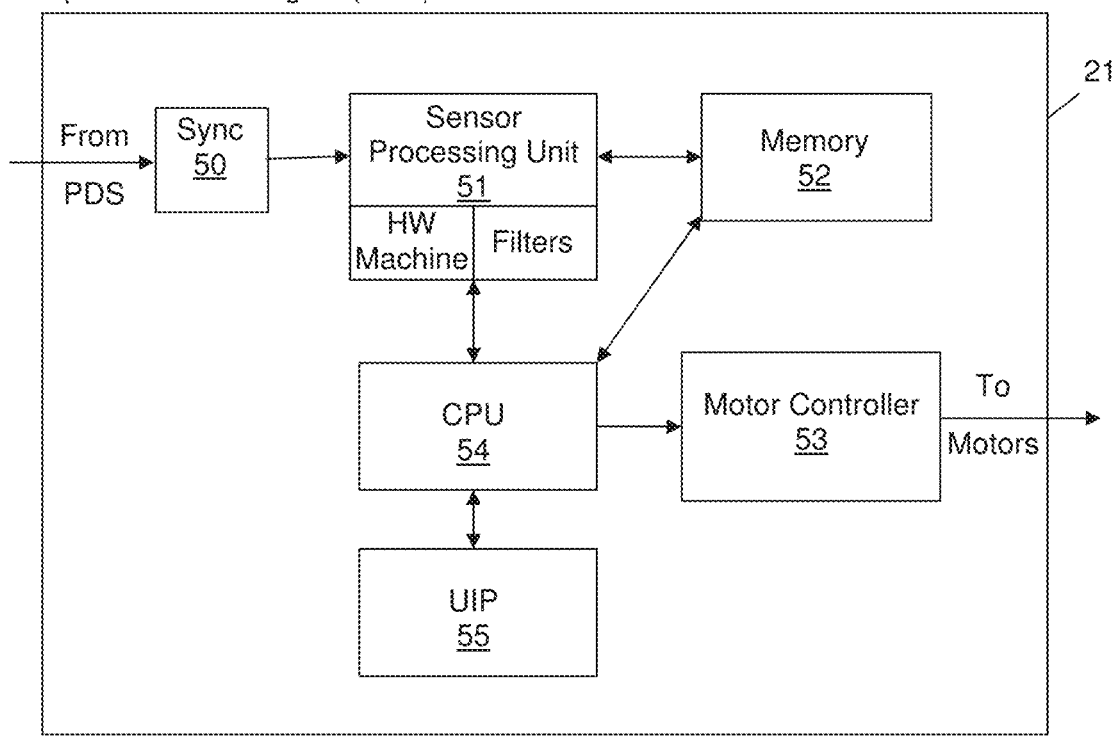
FIG. 6 schematically illustrates an exemplary top level plaque detection engine of the dental care device, according to an embodiment of the present invention.

FIG. 6 schematically illustrates an exemplary top level PDE in a block diagram from, according to an embodiment of the present invention.

As will be apparent to the skilled person, an input sync machine 50 can perform the alignment and synchronization on the data received from the PDS 18 incorporated in the plaque detection unit 13. For example, the data can be received in pixel clock rate and synced to the system clock using a FIFO line length buffer. Depending on the properties of PDS 18, the pixel data can be, for example, 8 bit width constituting a ~2K buffer (internal memory) for a 224×240 active pixel resolution. The active pixel data is then processed in pre-processing stages by a sensor processing unit 51 as described in further details hereinafter.

Processing Stages

The first stage of the pre-processing is a series of filters implemented in logic. The purpose is to reduce noise, eliminate motion blur, enhance luminance and prepare the data for generating a stitched picture where the advanced algorithms can be implemented on.

The second stage is hardware (HW) based feature detection machine, feature tracking and picture stabilization and stitching. This HW machines also use internal SRAMs for calculations and processing and perform the data extraction elements of the algorithms. In this stage specific teeth object recognition algorithms are also implemented. The stitched picture is then stored in a memory 52 for further processing.

The third part of the processing is done by a CPU 54 such as an ARM/Cortex processor. Using the data extracted by the HW machine the software enabled part of the algorithm is performed including locating the dental care device accurate coordinates, identifying the accurate plaque infected areas and outputting the commands to the plaque removal head of the dental care device.

A Motor Controller (MC) 53 translates the commands received from a motor movement calculation unit that resides in the ARM/Cortex processor to actual motor movements which control the plaque removal head. The MC 53 is also responsible for converting the bus interface and voltages to the dedicated motors that rotates/moves the array of bristles.

A User Information Processor (UIP) 55 is comprised of two main features generating video and audio user information. The UIP 55 produces user information needed at least for performing the cleaning. The UIP 55 may incorporate a video encoder module for video compression in order to forward video data to an external user screen, such as display unit 43 (FIG. 5).

The Audio generated information may include audible indication such as:

mouth section timer expiration;
brushing timer (e.g., 2 minutes);
misusage information;

The Video generated information may include visual indication such as:

mouth panoramic view (e.g., 8 sections);
specific section missed/under use indication;
pressure sensor indication;
replacement indication of the plaque removal head;
battery life information.

As aforementioned hereinabove, the motor is responsible for both the circular head movement and the sliding head movement according to the commands calculated by the PDE 21. The motor should be low power with a long life cycle to meet consumer products requirements.

The aforementioned embodiments provide a Smart toothbrush equipped with all necessary components to achieve perfect brushing. The Smart toothbrush offers a unique architecture combining semiconductor technology with video processing and delicate mechanics to deliver a Smart toothbrush paving the way to perfect brushing. Smart brushing is achieved by identifying the plaque infected areas of the tooth and working to relieve the detected plaque.

All the above description and examples have been given for the purpose of illustration and are not intended to limit the invention in any way. Many different mechanisms, methods of analysis, electronic and logical elements can be employed, all without exceeding the scope of the invention.

The invention claimed is:

1. A dental care device for detection and removal of plaque automatically and independently, comprising:
   a. a motion controlled plaque removal head having multiple arrays of bristles placed vertically and horizontally thereon, wherein each array of bristles is controlled separately by a dedicated motor;
   b. a plaque detection unit adapted to capture images of the teeth and gums, wherein said plaque detection unit includes an imaging device and a light source with specific wavelength for illumination of said teeth and gums; and
   c. a plaque detection engine adapted to process the captured images in order to accurately detect plaque infected areas on said teeth, and accordingly to generate instructions for automatically guiding said motion controlled plaque removal head to reach and focus on said infected areas and avoiding areas which do not need brushing, thereby enabling closing the loop between detecting the plaque residing areas and controlling the plaque removal head to reach them.

2. The dental care device according to claim 1, wherein the plaque detection unit is programmed to operate by applying hardware and/or software plaque finder algorithm(s).

3. The dental care device according to claim 2, wherein the plaque finder algorithm involves image processing, edge detection, and object detection.

4. The dental care device according to claim 1, further comprising a user information processor for providing video/audio user indications while using said device.

5. The dental care device according to claim 4, wherein the user indication includes real time brushing indications when user is asked to place the brush in a new location, timer, quality of brushing, percentage of plaque and over time improvement.

6. The dental care device according to claim 5, wherein a real time panoramic view of the entire mouth with color indications to the plaque location is presented for the user to follow while brushing.

7. The dental care device according to claim 1, wherein the multiple arrays of bristles are formed in a rounded manner, a linear manner or combination of both.

8. The dental care device according to claim 1, wherein the plaque removal head is longer than standard and having at least one flexible joint for enabling adjusting the shape of the plaque removal head to match the teeth line and brush several teeth simultaneously and one or more sensor devices for plaque detection.

9. The dental care device according to claim 8, wherein the movements of the flexible joints are passive and are depending only on the joint flexibility.

10. The dental care device according to claim 8, wherein the movements of the flexible joints are active by using one or more motors or actuators.

11. The dental care device according to claim 1, wherein the plaque detection engine eliminates abrasive application of the bristles by controlling the applied pressure, movements and avoiding places which do not need brushing.

12. The dental care device according to claim 1, wherein the plaque detection unit takes a continuous stream of images controlled by the plaque detection engine.

13. The dental care device according to claim 12, wherein the plaque detection unit receives the continuous stream of images and applies advanced picture processing algorithms on said received images, resulting in a set of commands to control the next movement performed by each array of bristles in conjunction with a movement of the head along an x-axis, thereby enabling, monitoring and controlling the operation of each dedicated motor whether it should be activated, stopped, accelerated or slowed.

14. A method of detection and removal of plaque automatically and independently, comprising:
   a) providing the dental care device of claim 1;
   b) capturing by the plaque detection unit of said device a continuous stream of images controlled by the plaque detection engine in communication with the motion controlled plaque removal head; and
   c) applying by said plaque detection engine an advanced picture processing algorithm on said captured images, resulting in a set of commands to control the next movement performed by each array of bristles in conjunction with a movement of said head along an x-axis, thereby enabling, monitoring and controlling the operation of each dedicated motor whether it should be activated, stopped, accelerated or slowed to reach and focus only on the contaminated areas.

15. The method according to claim 14, wherein movement of the head along the x-axis enables reference to specific coordinates and location.

16. The method according to claim 14, wherein the advanced picture processing algorithm includes primary picture processing starting from image stabilization and stitching algorithms followed by filtering, scaling, histogram construction and color manipulation.

17. The method according to claim 14, wherein the advanced picture processing algorithm includes teeth boundary detection by object edge detection, thereby eliminating abrasive application of the bristles on non-relevant areas.

18. The method according to claim 14, wherein the advanced picture processing algorithm further comprises looking for specific color deflection on the teeth boundaries detected.

19. The dental care device according to claim 1, further comprising at least one additional motor adapted to move the head for providing an additional degree of freedom to each of the multiple arrays of bristles, thereby allowing the bristles to move in any direction in two or more degrees of freedom.

* * * * *